United States Patent
Johnson et al.

(10) Patent No.: US 12,318,640 B2
(45) Date of Patent: Jun. 3, 2025

(54) FIREBREAK DEVICE

(71) Applicant: BPR MEDICAL LIMITED, Nottinghamshire (GB)

(72) Inventors: Benjamin Johnson, Nottinghamshire (GB); Martin Cooper, Nottinghamshire (GB); Michael Brudenell, Nottinghamshire (GB)

(73) Assignee: BPR MEDICAL LIMITED, Nottinghamshire (GB)

( * ) Notice: Subject to any disclaimer, the term of this patent is extended or adjusted under 35 U.S.C. 154(b) by 422 days.

(21) Appl. No.: 17/627,173

(22) PCT Filed: Jul. 16, 2020

(86) PCT No.: PCT/GB2020/051706
§ 371 (c)(1),
(2) Date: Jan. 14, 2022

(87) PCT Pub. No.: WO2021/009511
PCT Pub. Date: Jan. 21, 2021

(65) Prior Publication Data
US 2022/0280819 A1 Sep. 8, 2022

(30) Foreign Application Priority Data
Jul. 16, 2019 (GB) ..................................... 1910187

(51) Int. Cl.
*A62C 2/04* (2006.01)
*A61M 16/20* (2006.01)

(52) U.S. Cl.
CPC ............. *A62C 2/04* (2013.01); *A61M 16/208* (2013.01); *A61M 2205/3368* (2013.01)

(58) Field of Classification Search
CPC ... A62C 2/04; A62C 2/20; A62C 4/02; A61M 16/208; A61M 16/0816; A61M 16/201;
(Continued)

(56) References Cited

U.S. PATENT DOCUMENTS 1,022,119 A * 4/1912 Barton .................. F16K 17/383
137/75
2,048,387 A * 7/1936 Johnsen .............. F16L 55/1007
137/68.12
(Continued)

FOREIGN PATENT DOCUMENTS

| WO | 2008/075035 A1 | 6/2008 |
| WO | 2008068508 A1 | 6/2008 |
| WO | 2014/020334 A1 | 2/2014 |

*Primary Examiner* — Patrick C Williams
(74) *Attorney, Agent, or Firm* — Kaplan Breyer Schwarz LLP

(57) ABSTRACT

A firebreak device configured to arrest a flow of medical gas capable of combustion or of supporting combustion, said device comprising: a housing having a body portion, an inlet and an outlet, said inlet and outlet being linked by a conduit; a valve assembly located within said body portion, said valve assembly being movable between an open position, in which gas can flow between said inlet and outlet along said conduit, and a closed position in which gas flow between said inlet and said outlet is arrested; a biasing assembly (340) arranged within said body portion to move said valve assembly into said closed position; and a heat activatable stop (350) located between said biasing assembly and said outlet to hold said valve assembly in said open position against said biasing assembly, and adapted to release said valve assembly to allow said biasing assembly to move said valve assembly to said closed position at an activation temperature, to close flow of gas through the device if said heat activatable stop is activated, wherein: said heat activatable stop is arranged to prevent obstruction of said flow of gas adjacent an inner surface of said device.

18 Claims, 3 Drawing Sheets

(58) Field of Classification Search
CPC .......... A61M 16/20; A61M 2205/3368; A61M 2205/02; A61M 2202/0202; F16K 17/383; F16L 55/1022; F16L 55/1026; F16L 57/04
See application file for complete search history.

(56) References Cited

U.S. PATENT DOCUMENTS

| | | | |
|---|---|---|---|
| 2,048,389 A | | 7/1936 | Bjornulf |
| 2,707,965 A | * | 5/1955 | Allen .................... F16K 17/383 137/75 |
| 3,245,423 A | * | 4/1966 | Hansen .................. F16L 37/23 251/149.6 |
| 5,027,845 A | * | 7/1991 | Silagy .................... F16L 37/32 251/149.6 |
| 5,477,877 A | | 12/1995 | Schulze |
| 6,279,597 B1 | * | 8/2001 | Schulze ................ F16K 17/383 137/75 |
| 2013/0186494 A1 | * | 7/2013 | Geisel .................... F16L 37/23 137/798 |

\* cited by examiner

— 1 —

FIREBREAK DEVICE

FIELD OF THE INVENTION

Aspects and embodiments relate to a firebreak device. More particularly, aspects and embodiments relate to a clinical grade firebreak device configured for use with flexible tubing supplying medical or therapeutic gas capable of combustion or of supporting combustion and a method of forming such a clinical grade firebreak device.

BACKGROUND

Patients requiring therapeutic gas, for example, oxygen, may typically be administered such therapeutic gas via equipment such as a face mask or nasal cannula. That equipment is often connected to a gas source via flexible plastics tubing, and administration may occur in a domestic or clinical environment.

It has been established that the risk of fire when using such delivery apparatus with, for example, oxygen, oxygen enriched air, or any medical gas capable of supporting combustion, can be significant since the exposure of the apparatus to an ignition event can result in ignition. A flame which starts as an external fire supported by oxidising gases leaking from delivery apparatus may then move to the interior of the flexible plastics tubing from delivery equipment and migrate rapidly upstream towards the gas source.

The fire hazard resulting from the use of such gas delivery apparatus is exacerbated in a domestic environment because the use of the oxygen is not supervised by health care workers. The presence of mandatory smoke detectors, fire alarms and other such safety equipment cannot mitigate the risks due to the rapidity of spread of a fire in, for example, an oxygen rich environment, once triggered. The risk of catastrophic fires, especially due to careless use of such apparatus is higher in the case of patients who smoke since there is a temptation for a patient to discard the oxygen delivery mask or cannula, and leave it in the vicinity, still delivering therapeutic gas, whilst a cigarette is smoked. Most oxygen delivery apparatus is set to deliver oxygen continuously at a rate determined by the needs of the patient, and removal of the delivery interface from the patient airway does not cause the delivery of oxygen to cease. In such circumstances an oxygen-enriched atmosphere can build up around the patient thereby preparing ambient surroundings for a catastrophic conflagration upon ignition.

There is therefore a need for apparatus and/or procedures to prevent or avoid fires spreading if an ignition event occurs in the proximity of the patient using combustible gas delivery equipment in a clinical or domestic environment.

SUMMARY

Accordingly, a first aspect provides: a firebreak device configured to arrest a flow of medical gas capable of combustion or of supporting combustion, the device comprising: a housing having a body portion, an inlet and an outlet, the inlet and outlet being linked by a conduit; a valve assembly located within the body portion, the valve assembly being movable between an open position, in which gas can flow between the inlet and outlet along the conduit, and a closed position in which gas flow between the inlet and the outlet is arrested; a biasing assembly arranged within the body portion to move the valve assembly into the closed position; and a heat activatable stop located between the biasing assembly and the outlet to hold the valve assembly in the open position against the biasing assembly, and adapted to release the valve assembly to allow the biasing assembly to move the valve assembly to the closed position at an activation temperature, to close flow of gas through the device if the heat activatable stop is activated, wherein: the heat activatable stop is arranged to prevent obstruction of the flow of gas adjacent an inner surface of the device.

It is known that it is desirable to ensure any device placed in a therapeutic gas path introduces minimal backpressure into that flow of gas, thus ensuring that a selected flow of gas actually reaches a patient. Ensuring gas can flow freely through the central portion of a channel or device helps to ensure back pressure is minimal. Forcing gas flow along the inner surfaces of the device introduces greater resistance to gas flow and therefore undesirable backpressure. The first aspect recognises that, contrary to such an approach, ensuring reliable operation of a firebreak device can be aided by forcing gas flow towards inner surfaces of the device. Furthermore, arranging the fusible stop such that the gas flow along the inner surfaces of the device, and/or on exit from the device, in the region of the fusible stop, is minimally disrupted can aid in reliable operation of the fusible stop and therefore the firebreak device. Aspects recognise that reliability of operation of the fusible stop may be particularly affected by location of flow of therapeutic gas in the region of the stop at low gas flow rates, and that back pressure issues may also be of significance at such low gas flow rates.

Accordingly, aspects provide firebreak devices in which the heat activatable stop is arranged to prevent obstruction of the flow of gas adjacent an inner surface of the device. In other words, the fusible stop is dimensioned or positioned within the firebreak device such that flow of gas adjacent an inner surface of the device is minimally obstructed. According to some aspects, the fusible stop may be arranged to occlude a central portion of a gas flow path through a firebreak device.

According to some embodiments, the heat activatable stop is dimensioned to prevent obstruction of the flow of gas adjacent an inner surface of the device. According to some embodiments, the heat activatable stop is shaped to prevent obstruction of the flow of gas adjacent an inner surface of the device. According to such arrangements, a fusible stop may allow or encourage gas flow adjacent the inner surface of the device and occlude gas flow in a central region of the device.

According to some embodiments, the heat activatable stop contacts and occludes less than 25% of an inner circumference of the device at the position of the heat activatable stop. According to some embodiments, the heat activatable stop contacts and occludes less than 15% of an inner circumference of the device at the position of the heat activatable stop. According to some embodiments, the heat activatable stop occludes less than 30% of an inner cross-sectional area of the device at the position of the heat activatable stop. It will be appreciated that the more open the conduit is, the less the stop occludes the lumen through which the gas flows, the lower a therapeutic gas flow can be, whilst obtaining reliable activation of the fusible stop and successful firebreak operation.

According to some embodiments, the heat activatable stop is shaped to direct trajectory of the gas flow towards the inner surface of the device. Such shaping may, for example, comprise one or more tapered elements. According to some embodiments, the heat activatable stop is shaped or arranged to occlude a central region of the conduit.

According to some embodiments, the heat activatable stop comprises: an axle arranged to occlude the central region of the conduit. According to some embodiments, the heat activatable stop comprises: a plurality of spokes extending between the axle and the inner surface of the device.

According to some embodiments, the heat activatable stop is located to prevent obstruction of the flow of gas adjacent an inner surface of the device. Accordingly, some embodiments recognise that it may be desirable to locate the fusible stop within the firebreak device, rather than at one end of the device, thereby allowing greater control of a fire approaching the fusible stop. Such control may include control of fuel to the fire, and/or conduit surface leading to the fusible stop. According to some embodiments, the heat activatable stop is located between the body portion and the outlet. According to some embodiments, the inner surface of the device includes one or more burn rib formed on the inner surface of the device, the burn rib being located between the heat activatable stop and the outlet. Provision of burn ribs can help to control tracking of a fire to the fusible stop, even at low gas flow rates. According to some embodiments, the burn rib extends along the inner surface in an axial direction between the heat activatable stop and the outlet. According to some embodiments, the burn rib extends from a support of the heat activatable stop to the outlet. Accordingly, a fire tracking along tubing to which the device is connected may track back into the firebreak device and directly to the fusible stop, along the burn rib(s). The burn rib(s) may preferentially burn compared to the rest of the inner surface of the device, particularly at low rates of gas flow.

According to some embodiments, the heat activatable stop is integrally formed with a region of the conduit in which it is located.

According to some embodiments, the heat activatable stop comprises: a plurality of radial supports spanning the outlet, the radial supports being dimensioned to prevent the gas flow in a central region of the outlet and allow substantially free gas flow around a periphery of the outlet when the valve assembly is in the open position.

According to some embodiments, the heat activatable stop spans an inner diameter of the device and comprises at least two orifices adjacent the inner surface of the device which direct a trajectory of gas flow towards the inner surface of the device. The heat activatable stop may comprise a diaphragm, thin sheet of material forming a partition, web or net spanning the inner diameter of the device. The diaphragm may comprise an occluded central portion and two or more orifices, slots or holes immediately adjacent the inner surface of the device. Provision of slots, orifices or holes adjacent an inner surface of the device may help to ensure gas flow is directed towards the inner surface of the device. As a result, a flow of gas capable of supporting combustion along the inner surface of the device is supported. That flow of gas may help to ensure combustion in the region of the heat activatable stop is supported.

According to some embodiments, the heat activatable stop is located within the device between the body portion and said outlet. The heat activatable stop may be recessed within the device, inset from said outlet. Accordingly, by locating the heat activatable stop away from a transition between the device outlet and an environment outside the device, for example, flexible tubing into which the device may be placed, it is possible to ensure that gas flow in the region of the heat activatable stop is more closely controllable, since it is less impacted by external factors.

According to some embodiments, a firebreak device is provided comprising an elongate sacrificial burn portion located between the heat activatable stop and said outlet. In other words, the device may include a sacrificial portion, which may itself burn or melt before the heat activatable stop causes activation of the valve assembly. Embodiments recognise that by providing a sacrificial burn portion between a distal end of the device and the heat activatable stop it is possible to improve control of activation of the heat activatable stop. Such an arrangement, coupled with insetting or recessing the heat activatable stop may ensure that interruption of gas flow in the region of the outlet of the device may be minimally impacted on transition to an environment outside the device. Provision of a heat activatable stop at the distal end and as part of the outlet itself may require the end of the device to have a thickness or ledge which acts to disrupt gas flow. By moving the stop inside the device, the device wall in the region of the outlet may be reduced or thinned such that any step which occurs between an inner surface of the device and an environment outside the device is limited by the properties of the material forming the device.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which.

DESCRIPTION OF THE EMBODIMENTS

Patients requiring therapeutic gas, for example, oxygen, may typically be administered that therapeutic gas via equipment such as a face mask or nasal cannula. That equipment is often connected to a gas source via flexible plastics tubing, and administration may occur in a domestic or clinical environment.

A therapeutic gas supply line from a gas source to a patient typically comprises flexible plastics tubing, for example, polythene or a similar plastics material.

Figure 1A:
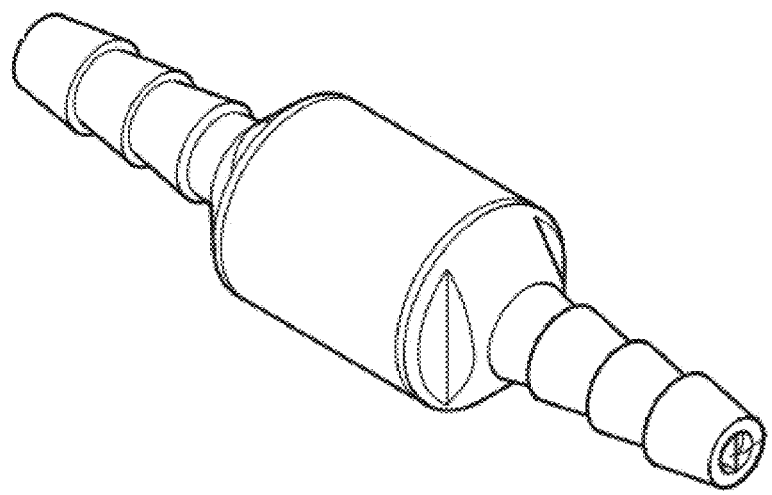
FIG. 1a and FIG. 1b illustrate schematically example firebreak devices in which arrangements described may find application.
Figure 1B:
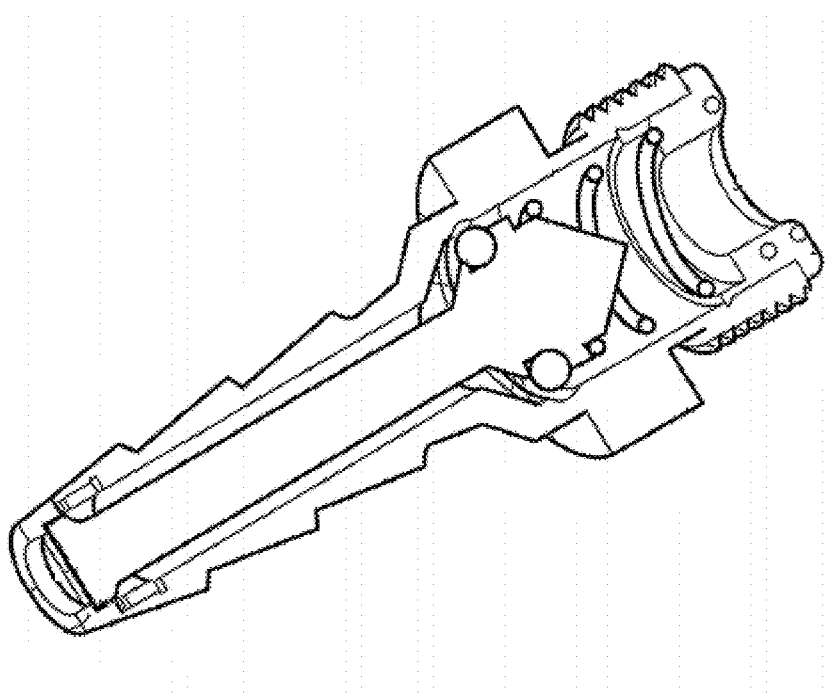

FIG. 1a and FIG. 1b illustrate schematically example firebreak devices in which arrangements described may find application. FIG. 1a shows one example of a firebreak device in which one or more of the inlet and outlet nozzle openings in accordance with described arrangements may find particular application. The firebreak device shown in FIG. 1a comprises a bidirectional in-line firebreak device. The operation of such a device is described in more detail, for example, in WO2014/020334. Such devices are such that both inlet and outlet are connectable to flexible tubing through which therapeutic gas flows for delivery to further apparatus or to a patient. FIG. 1b shows one example of a firebreak device in which an outlet nozzle opening in accordance with described arrangements may find particular application. The firebreak device shown in FIG. 1b comprises a unidirectional firebreak device attachable directly to gas delivery apparatus including an outlet nozzle portion directly connectable to flexible tubing through which therapeutic gas may flow and an inlet portion directly connectable to gas delivery apparatus, for example, a regulator or gas supply. The operation of such devices is described in more detail, for example, in WO2008/075035.

In both types of firebreak device, general operation is substantially the same. Namely: a firesafe medical gas device connectable to flexible tubing supplying medical gas capable of combustion or of supporting combustion is provided. The device operates to arrest a flow of medical gas capable of combustion or of supporting combustion, and generally comprises a housing having a body portion, an inlet and an outlet. The inlet and outlet are usually linked by a conduit of some kind, through which gas may be able to flow. The devices include a valve assembly located within the body portion. The valve assembly is movable between an open position, in which gas can flow between the inlet and outlet along the conduit, and a closed position in which gas flow between the inlet and outlet is arrested. Valve operation is secured by provision of a biasing assembly arranged within the body portion. The biasing assembly is configured to urge the valve assembly into the closed position. The firesafe nature of the firebreak devices is provided by an appropriate heat activatable stop, typically located between the biasing assembly and the outlet. The heat activatable stop acts to hold the valve assembly in the open position against the exertion of biasing force by the biasing assembly. The stop is adapted to release the valve assembly and allow said biasing assembly to move said valve assembly to said closed position. In particular, the stop is formed from a material and/or dimensioned and/or located such that, at a predetermined activation temperature (such as a temperature associated with exposure to a fire associated with combustion of materials fed by said therapeutic gas, or the temperature and timing associated with flashback) the stop no longer acts against the biasing assembly. As a result, the valve assembly moved towards the closed position and closes any flow of gas through the device. That is to say, the existence of a fire or flashback event associated with said therapeutic gas capable of combustion, or of supporting combustion, causes the heat activatable stop to be activated, and no longer perform the "stopping" function.

Figure 2:
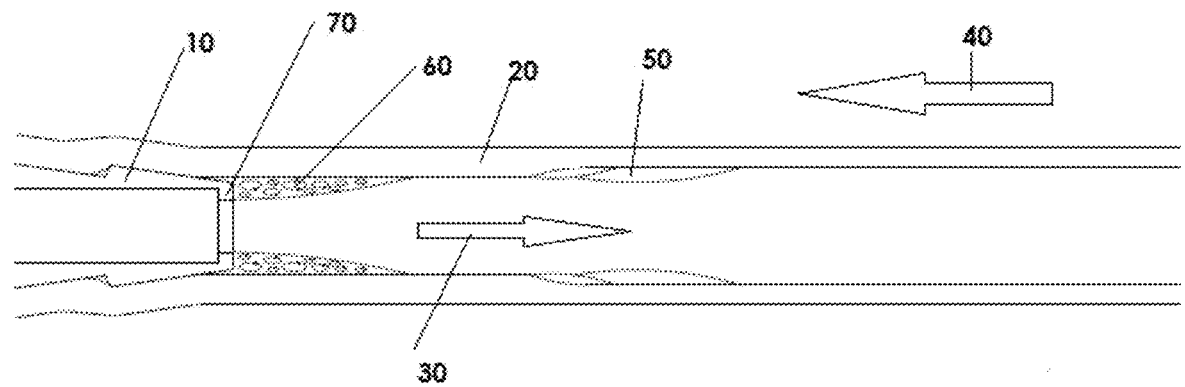
FIG. 2 illustrates schematically some main features which can occur in the event of a fire in the region of a firebreak device such as those shown generally in FIG. 1a and FIG. 1b.

FIG. 2 illustrates schematically some main features which can occur in the event of a fire in the region of a firebreak device such as those shown generally in FIG. 1a and FIG. 1b. As shown in FIG. 2, a nozzle portion 10 of a firebreak device similar to those shown in FIG. 1a and FIG. 1b has been inserted into a portion of flexible gas tubing 20. The nozzle portion 10 is in a substantially gas-sealed friction fit with the tubing 20. A flow of gas 30 passes from a gas supply, through the firebreak device, out of nozzle 10 and along tubing 20 in the direction of arrow 30 towards further equipment and ultimate delivery to a patient. In the event a fire, an initiating event will typically occur downstream of the gas supply and track back, in the opposite direction of arrow 40 towards the gas supply. The fire is supported by combustion of, for example, an inner surface of the flexible plastic gas tubing 20. Temperature inside the tubing in the event of fire causes a region of vaporised polymer in the inner surface of the tubing, which combusts in area 50, as supported by the presence of the therapeutic gas. If operating correctly, a fire will track back along tubing 20 to the firebreak device nozzle 10. A ledge 70 provided at the end of the nozzle 10 often acts as at least part of the heat activatable stop referred to previously. The ledge 70 softens or melts on exposure to fire and/or hot exhaust gases, and activates. Activation of the stop means the valve assembly can no longer be held in an open position against force from the biasing assembly, and the valve assembly moves to a closed position. In the closed position, the firebreak device arrests any further gas flow beyond the firebreak device.

It has been found that configuration of devices as shown in FIG. 2 can suffer from poor reliability. In particular, it can be observed that firebreak device valve closure may fail to occur in the event of a tubing fire at low oxygen flow rates. It has been found that a length of tubing, for example, flexible PVC tubing, greater than around 250 mm provided after the firebreak device may increase chances of firebreak device failure. It was observed that in such a low oxygen flow rate arrangement, a fire was often extinguished before a fusible stop provided as part of the device had been activated, thus allowing therapeutic gas capable of combustion or of supporting combustion to continue to flow from source into the surrounding environment, in which secondary fires may exist.

It has also been found that in examples of oxygen delivery scenarios, when oxygen flow rates are between 0.25 and 2.00 l/min, and a gas delivery path exists in which lengths of plasticised PVC tubing longer than about 300 mm are provided, conventional firebreak devices may operate to extinguish a fire but fail to fully isolate oxygen flow rate. It has been found that firebreak device failure rate increases with reducing oxygen flow.

Possible causes of firebreak failure modes have been studied. It has been found that it is typical for material forming the flexible gas delivery tubing to provide fuel supporting any fire. This is aided by the provision, within the tubing, of an oxygen rich therapeutic gas environment. It will be appreciated that waste products are formed by the combustion process. In the case where a short length of tubing is provided between a firebreak device and delivery to a patient, and a fire occurs in that length of tubing, the waste exhaust products can escape from the confines of the length of tubing at the tubing end (ie in the region of the patient). Where a long length of tubing is provided between the firebreak device and delivery to a patient, waste products no longer have an easy exit path from the confines of the tubing. Ash and char build up on the inner tubing surface and may form partial or full occlusions in the tubing. Such occlusions can lead to pressure build up inside the tubing and consequent burst through. The path of a fire along a length of tubing may, in such instance, be unpredictable. It will be appreciated that if the fire does not reach a length of tubing adjacent a provided firebreak device, and more particularly, the heat activatable stop of the firebreak device, then the firebreak device will not operate as reliably as intended.

Furthermore, it has been found that flow of therapeutic gas, for example, oxygen, in the region of an exit from the firebreak device can impact upon successful operation of the firebreak. As shown in FIG. 2, as gas flows from nozzle 10 into tubing 20, a turbulent region of gas flow occurs 60. That turbulent region includes gas eddies and comprises a non-laminar gas flow. As shown schematically in FIG. 2, on exit from the nozzle of the firebreak device, laminar gas flow is more likely to be achieved in the central portion of the tubing, rather than in the regions of tube lumen immediately adjacent the inner surface of the tubing. As a result, combustion of vaporised tubing material 50 is disrupted and tracking of a fire along tubing back towards a gas supply may be arrested before the fire reaches the firebreak device.

It has been found that factors which impact upon successful firebreak operation can depend upon a range of contributing factors. For example, intensity of combustion in a scenario such as that illustrated by FIG. 2 may depend upon: the temperature of combustion (burn temperature) of tubing material, oxygen (or oxygen enriched air) flow rate into the tubing, and similar. In relation to tubing material and a mix of oxygen or oxygen enriched air, different tubing and flow configurations can lead to variations in combustion conditions. There will typically be a rich (upper flammable limit) and lean (lower flammable limit) combustion gas mixture which allows for smooth progress of a fire back along tubing towards a firebreak device. It will be appreciated that the combustion gas mixture can be affected by system geometry, for example, diameter of tubing may be a factor, obstructions may build up within tubing to form obstructions and consequent pockets of stagnant gas which may block or interrupt smooth tracking of a fire along tubing towards a firebreak device. Slow or stagnant pockets of gas or gas/fuel mixture can extinguish the fire. In particular, it has been recognised that when the propagation of the fire is paused or slowed, exhaust gases build around an area under combustion and the mixture can become too lean to support successful combustion with the consequence that the fire stutters and then goes out.

Arrangements seek to ameliorate some factors which may impact upon tracking of a fire towards a gas supply, via a heat activatable stop of a firebreak device.

Arrangements described recognise that one possible route to improve firebreak device reliability is to arrange component parts of the firebreak device to minimally disrupt flow of gas through the firebreak device conduit in the case the valve assembly is in the open position. That is to say, to arrange components of the firebreak device such that they achieve a similar resistance to a flow of gas therethrough as an equivalent length of tubing. Arrangements described further recognise that as a fire tracks back towards a gas source, a primary source of fuel can be the tubing and firebreak device. In particular an inner surface of the tubing and firebreak device. Arrangements described recognise that it may be beneficial to arrange one or more components of the firebreak device such that flow of therapeutic gas which supports combustion remains substantially laminar rather than turbulent adjacent an inner surface of firebreak and tubing. Arrangements may seek to manage and direct a flow of therapeutic gas such that a substantially laminar flow of gas along an inner surface of the firebreak device, tubing and any transition between such components is maintained. Arrangements recognise that encouraging gas flow to "stick" to an inner surface of the firebreak device conduit and/or outlet, particularly in the region of the heat activatable stop, can assist with reliable operation of the firebreak device.

Figure 3:
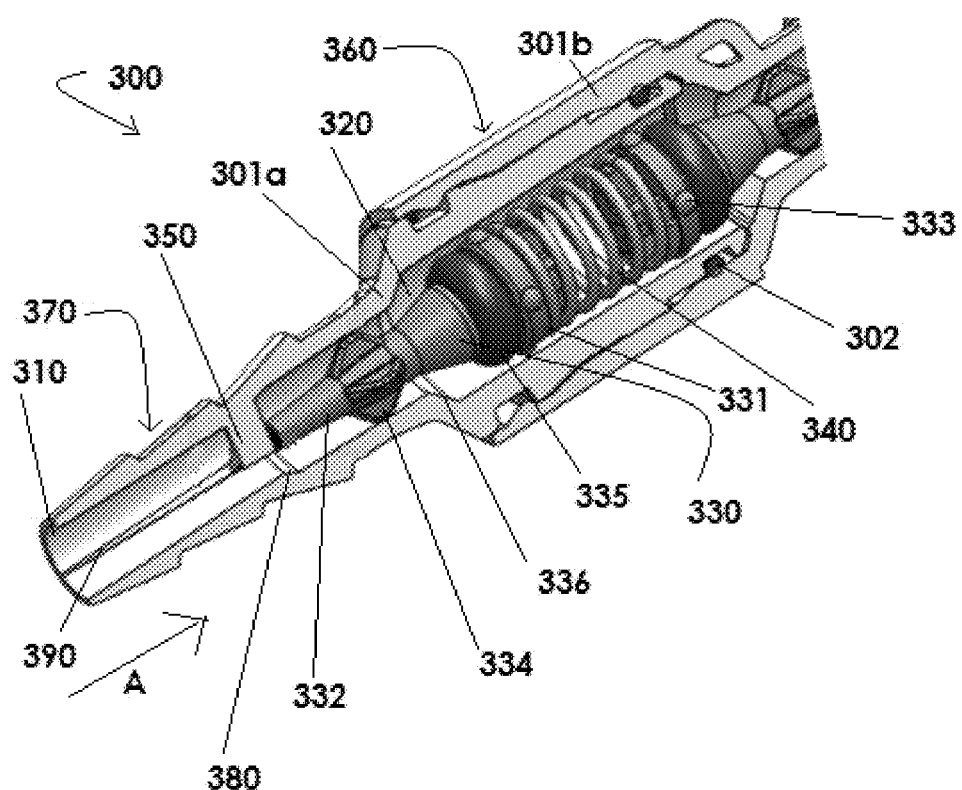
FIG. 3 illustrates schematically a cut-away cross-sectional view of a firebreak device according to one possible arrangement.

FIG. 3 illustrates schematically a cut-away cross-sectional perspective view of a firebreak device according to one possible arrangement. The device of FIG. 3 is suitable for insertion into a typical gas supply line (not shown). The gas supply line may comprise appropriate flexible plastics tubing.

The firesafe device 300 shown in FIG. 3 takes the form of a bidirectional in-line firebreak device, meaning that it is directly insertable into a flexible gas tubing supply line. It will be appreciated that the approach and features described in relation to one end of the bidirectional device shown may be applied to one or both ends of the device, and that approaches and features described may be applied to unidirectional in-line firebreak devices and to firebreak devices provided for direct connection to ancillary gas delivery apparatus and equipment.

The firebreak device 300 comprises generally: a body having an opening 310 at each end (only one end shown in FIG. 3). Those openings serve as an inlet and outlet for therapeutic gas into the device 300. The inlet and outlet openings 310 are linked by a flow path, in the general form of a conduit 320. A valve assembly 330 is located within the device body. The valve assembly is movable between an open position, in which gas can pass between the inlet and outlet along said conduit, and a closed position in which gas flow between the openings is prevented. The device 300 also comprises a biasing assembly 340 arranged within the device body to urge the valve assembly towards the closed position. The device also includes a heat activatable stop 350 located between the valve assembly and the opening 310 forming an outlet for gas from the device 300. The heat activatable stop 350 is operable to hold the valve assembly 330 in the open position against the natural action of the biasing assembly 340 and is arranged to release the valve assembly on exposure to a fire at a preselected activation temperature, thereby allowing the biasing assembly 340 to move the valve assembly 330 to the closed position. The particular arrangement of components of the firebreak device 300 in the region of the heat activatable stop will be described in more detail below.

FIG. 3 shows one example interior structure of a firesafe device, the general operation of which will be described further. It will be understood, however, that other interior configurations of a firesafe device are possible and that the particular arrangement and operation of components of a firebreak device in the region of the heat activatable stop can be adapted to accommodate such alternative interior configurations.

In the arrangement shown in FIG. 3, the in-line firebreak device body is generally elongate and comprises a hollow bulbous central portion 360 from which tapered nozzle portions 370 project (only one shown in FIG. 3). The firebreak device body is formed from two halves 301a, 301b which snap fit together. Those halves each have an elongate nozzle connector which extend from the hollow bulbous central portion. In order to ensure the join between the two halves 301a, 301b is gas tight, a sealing ring 302 is provided. Such a sealing ring 302 may be formed from an appropriate sealing material, for example, rubber, and may be substantially annular.

FIG. 3 shows that nozzle connectors 370 include tapered external ridges of increasing diameter as proximity to the central bulbous portion increases. Those ridges assist in creating a friction fit, gas tight engagement between the device 300 and an interior surface of flexible tubing for gas delivery.

As described previously, the nozzle portion extends to an opening 310. The opening may comprise the inlet or outlet to the bidirectional device shown in FIG. 3. The inlet and outlet are linked via a flowpath, which passes along the length of the body of the device when in position in a gas supply line and whilst the valve assembly described in detail below is in the open position.

The central portion of the device 300 houses a biasing assembly 340 in the form of a spring. That spring is configured to urge the valve assembly 330 towards a position in which the valve assembly prevents gas flow through the device. In the arrangement shown in FIG. 3, the valve assembly comprises a generally tapered element which extends from the central portion of the device into the nozzle connector. The generally tapered element comprises a head 331 from which extends a tail 332. The head and tail of the valve assembly are dimensioned such that they predominantly have an outer diameter less than an inner diameter of the body and nozzle connector whilst the valve assembly is held in the open position. In other words, gas can flow between the outer surface of the valve assembly and the inner surface of the device body and nozzle. In the example shown in FIG. 3, the valve assembly includes alignment projections in the form of small bump protrusions 333 on the head of the valve assembly and radially extending fins 334 on the tail of the valve assembly. Those alignment projections are arranged around the circumference of the valve assembly and dimensioned to contact the inner surface of the device body and nozzle connector respectively. The alignment projections 333 and 334 contact the inner surface of the device body whilst the valve assembly is both in the open and closed positions. The alignment protrusions 333 and 334 help to ensure smooth and reliable operation of the valve. The alignment features help to keep the valve assembly concentric within the device and help to prevent device misassembly. It will be appreciated that the alignment protrusions are dimensioned and shaped to minimally disrupt gas flow through the firebreak device when the valve assembly is in the open position. The presence of the alignment protrusions helps to ensure that the valve assembly abuts heat activatable stop 350 in a secure manner when the valve assembly is in the open position. Misalignment of the valve assembly with respect to the stop 350 may cause inappropriate activation of the valve. Secure and precise alignment as a result of the alignment protrusions may help to ensure that the dimensions of the stop can be selected to be smaller, and thus more sensitive to exposure to heat, such as that encountered in the event of a fire.

The head 331 of the valve assembly in the embodiment shown includes a shoulder portion or ledge against which the spring 340 exerts a force to urge the valve assembly into a closed position. The head also includes a circumferential groove which receives an annular o-ring 335. That resilient annular o-ring 335 abuts a conically tapering ledge forming an annular valve seat 336 formed on an internal surface of the hollow bulbous portion of the device body. The resilient sealing O-ring 335 seals against shoulder 336 in the event that the thermally activated stop 350, described further below, is activated due to exposure to excessive heat, for example, due to fire or explosion in its vicinity.

In some embodiments, a foot of a valve piece bears against a rim or inwardly projecting lip provided in the region of inlet and/or outlet openings. The combination of the foot and the lip acts as a thermally fusible, heat activatable stop to retain valve apparatus in an open position, working against a biasing mechanism, for example, in the form of spring or springs provided to urge the valve apparatus into a closed position.

Figure 4:
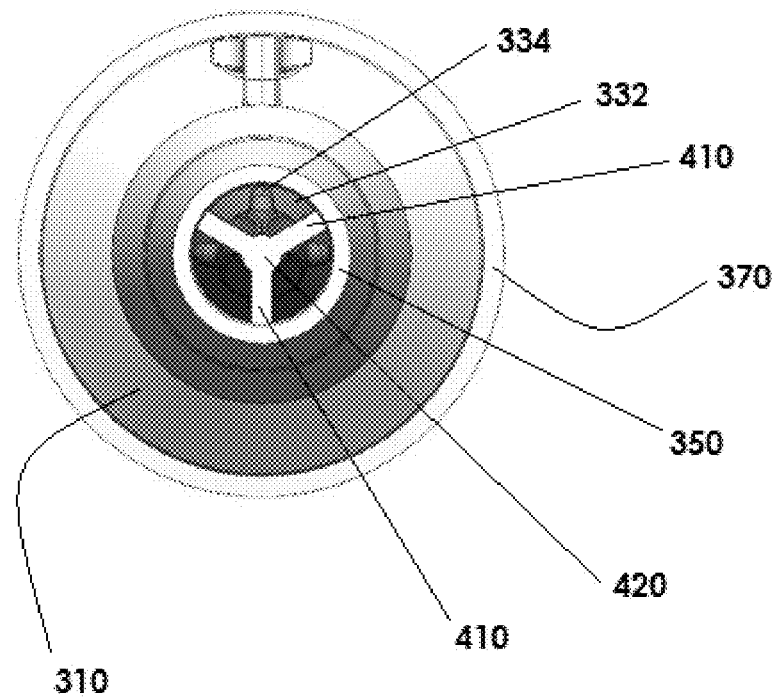
FIG. 4 is a view along the firebreak device nozzle connector of FIG. 3 in the direction of arrow A.

FIG. 4 is a view along the firebreak device nozzle connector of FIG. 3 in the direction of arrow A. Features and operation the heat activatable stop 350 will now be described further with reference to FIGS. 3 and 4. In the embodiment shown in FIGS. 3 and 4, the stop 350 is located within the nozzle connector 370. It is recessed from the outlet opening 310. The inner bore of the nozzle connector changes in the region of the stop 350. The change in inner bore diameter occurs smoothly as a result of a sloping shoulder 380. Such a smooth transition can help to ensure flow of gas through device 300 remains smooth and that the gas flow occurs smoothly along the inner surfaces of the body and nozzle connectors of the device. The inner bore of the nozzle connector in the arrangement shown in FIG. 3 includes a plurality of burn ribs 390, projecting slightly from the smooth inner surface of the bore and, in the arrangement shown, aligning with a part of the stop 350 which extends to the inner bore of the nozzle portion. Those ribs may help very low energy flames to track to the heat activatable stop rather than being extinguished before reaching it. At a very low gas flow rate, for example 0.25 l/min, only the ribs burn on approach to the stop.

In the example shown it will be appreciated that the heat activatable stop is not located at the device outlet, but instead is set back from that outlet. In this case, the region downstream of the heat activatable stop can be more closely controlled in the event of a fire. For example, rather than the flexible tubing leading to the heat activatable stop, a region of device leads directly to the heat activatable stop. Setting back the heat activatable stop ensures that the fuel to the fire is controlled at the critical activation step. In the example shown the heat activatable stop may be formed from a polyamide which burns very cleanly and predictably and produces very little char.

In the example shown in FIGS. 3 and 4, the stop 350 takes the form of three radial spokes 410 projecting from a central axle 420. The axle 420 provides a support against which the valve assembly bears to retain the valve apparatus in an open position, the stop 350 working against the spring 340 provided to urge the valve assembly into a closed position. According to arrangements, the stop 350 is formed of a material which is sensitive to heat and softens or fuses at the temperatures such as may be caused by flashback and/or ignition of a therapeutic medical gas. That material must also have sufficient strength that, in use, it retains its structural integrity within the nozzle connector against the compressive force of the spring acting thereon. Suitable materials include some thermoplastics such as, for example, polyvinylchloride (PVC), and materials such as waxes and lead free solder. The tri-leg design of the stop ensures that trajectory of gas flow in the region downstream of the stop is directed towards the device or tubing walls instead of being concentrated in the centre of the tubing. Width and thickness of the spoke supports of the stop can be optimised to balance resistance to flow and overall strength. For example, the thickness of the stop in the example shown may be in the region of 1.9 mm thus increasing the second moment of area and therefore stiffness against the opposing axial load applied by the biasing assembly to reduce the risk of premature activation. The width of the supports, however, may be significantly less, to impede gas flow minimally.

It has been found that sensitivity and reliability of a firebreak device such as the one shown in FIGS. 3 and 4 can be improved by taking steps to ensure gas can flow freely through the device when it is in an open position. Components of the firebreak device can be arranged to provide a consistent cross-sectional area throughout the device for gas flow. That cross-sectional area may be provided predominantly adjacent an inner surface of the device. Consistent gas flow against an inner surface can help to ensure a smooth laminar gas flow through the device and on exit from the device. Such an arrangement of components can help to minimise backpressure and resistance to gas flow introduced by the device.

It has also been found that more tightly controlling a gas flow path in the region of the heat activatable stop 350 can assist in ensuring reliable operation of the device across a range of gas flow rates.

Adults are commonly prescribed home oxygen at 1 l/min or more whereas flow rates as low as 0.1 l/min or even less might be prescribed to infants and paediatric patients. In the event of a fire, in order for combustion to progress along flexible gas delivery tubing, the material from which the tubing is formed (typically solid PVC, and the plasticiser bound within it) melts and is vaporised to form a gaseous fuel mixture. The fuel mixture combines with therapeutic gas capable of supporting combustion, for example, oxygen or oxygen enriched air, flowing through the tubing from a source. That combination allows a fire to progress and track back towards a gas source along the delivery tubing. Provided the fuel and oxygen mixture remains within bounds of upper and lower flammability limits, a fire can continue to progress along the tubing.

A number of factors impact upon fire progress and upon operation of a firebreak device such as the one shown in the Figures:

Provision of a stop which disrupts airflow along the surface of an inner bore of the nozzle portion can lead to a turbulent eddy forming downstream of the fusible stop, thereby preventing fresh oxygen or oxygen enriched gas flowing into a space adjacent the stop. That space is key to where combustion must progress to enable a transition of a fire from consuming flexible tubing to consuming, and therefore activating, the heat activatable stop. The turbulent eddy tends to recirculate gases within the eddy and thereby prevent fresh fuel or oxygen from entering that volume. As a fire fed by a low oxygen flow rate, such as 1 l/min or less, progresses into the volume of the turbulent eddy, the vaporised fuel mixture tends to extinguish since the mixture becomes too rich to burn.

With oxygen flow rates of around 2 l/min or less, there is a tendency for a pause in the progression of the approaching fire as it reaches the fusible ledge caused by the turbulent flow of gas downstream of the fusible stop. Often the fire is extinguished before the heat activatable stop has been consumed, thereby failing to activate the valve and isolate the oxygen flow.

It has also been recognised that as combustion continues along flexible tubing towards a source of oxygen or oxygen enriched air, gaseous by-products of combustion flow out of a downstream end of tubing. Some soot and carbonaceous char is deposited along the inside of the tubing, which can cause some flow resistance.

Arrangements seek to mitigate chances of failure of firebreak devices, allowing for successful isolation of therapeutic gas, for example, oxygen flow, if a fire occurs. Arrangements seek to provide a firebreak device which can operate with high levels of confidence and reliability across a full range of flow rates.

It has been found that consideration of open flow area (in mm$^2$) at a cross sectional area where the stop is located in the device divided by the fusible stop ledge contact length (in mm) around the device inner bore circumference (in mm) can provide an indicator of how effectively a firebreak may operate to activate in the event of a fire. In particular, it has been found that a firebreak device may operate successfully if flow area to edge length is less than about 0.6 mm, improved operation may occur if flow area to edge length less than about 0.5 mm and that most effective operation can be found if flow area to edge length less than about 0.4 mm.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:

1. A firebreak device configured to arrest a flow of medical gas capable of combustion or of supporting combustion, said device comprising:
   a housing having a body portion, an inlet and an outlet, said inlet and outlet being linked by a conduit;
   a valve assembly located within said body portion, said valve assembly being movable between an open position, in which gas can flow between said inlet and outlet along said conduit, and a closed position in which gas flow between said inlet and said outlet is arrested;
   a biasing assembly arranged within said body portion to move said valve assembly into said closed position; and
   a heat activatable stop located between said biasing assembly and said outlet to hold said valve assembly in said open position against said biasing assembly, and adapted to release said valve assembly to allow said biasing assembly to move said valve assembly to said closed position at an activation temperature, to close flow of gas through the device if said heat activatable stop is activated;
   and said heat activatable stop is arranged to prevent obstruction of said flow of gas adjacent an inner surface of said device; and wherein
   said inner surface of said device includes one or more elongate burn rib formed on said inner surface of said device, said burn rib being located between said heat activatable stop and said outlet, and said elongate burn rib has its elongate dimension arranged to extend along the inner surface in an axial direction between said heat activatable stop and said outlet.

2. A firebreak device according to claim 1, wherein said heat activatable stop is dimensioned to prevent obstruction of said flow of gas adjacent an inner surface of said device.

3. A firebreak device according to claim 1, wherein said heat activatable stop contacts and occludes less than 25% of an inner circumference of said device at the position of said heat activatable stop.

4. A firebreak device according to claim 1, wherein said heat activatable stop contacts and occludes less than 15% of an inner circumference of said device at the position of said heat activatable stop.

5. A firebreak device according to claim 1, wherein said heat activatable stop occludes less than 30% of an inner cross-sectional area of said device at the position of said heat activatable stop.

6. A firebreak device according to claim 1, wherein said heat activatable stop is shaped to direct trajectory of said gas flow towards said inner surface of said device.

7. A firebreak device according to claim 1, wherein said heat activatable stop is arranged to occlude a central region of said conduit.

8. A firebreak device according to claim 1, wherein said heat activatable stop comprises: an axle arranged to occlude said central region of said conduit.

9. A firebreak device according to claim 8, wherein said heat activatable stop comprises: a plurality of spokes extending between said axle and said inner surface of said device.

10. A firebreak device according to claim 1, wherein said heat activatable stop is located to prevent obstruction of said flow of gas adjacent an inner surface of said device.

11. A firebreak device according to claim 1, wherein said heat activatable stop is located between said body portion and said outlet.

12. A firebreak device according to claim 1, wherein said burn rib extends from a support of said heat activatable stop to said outlet.

13. A firebreak device according to claim 1, wherein said heat activatable stop is integrally formed with a region of said conduit in which it is located.

14. A firebreak device according to claim 1, wherein said heat activatable stop comprises: a plurality of radial supports spanning said outlet, said radial supports being dimensioned to prevent said gas flow in a central region of said outlet and allow substantially free gas flow around a periphery of said outlet when said valve assembly is in said open position.

15. A firebreak device according to claim 1, wherein said heat activatable stop spans an inner diameter of said device and comprises at least two orifices adjacent said inner surface of said device which direct a trajectory of said gas flow towards said inner surface of said device.

16. A firebreak device according to claim 1, wherein said heat activatable stop is located within the device between said body portion and said outlet.

17. A firebreak device according to claim 1, wherein said heat activatable stop is recessed within the device inset from said outlet.

18. A firebreak device according to claim 1, comprising an elongate sacrificial burn portion located between said heat activatable stop and said outlet.

* * * * *